(12) United States Patent
Byun et al.

(10) Patent No.: US 6,589,943 B2
(45) Date of Patent: Jul. 8, 2003

(54) FORMULATION OF AMPHIPHILIC HEPARIN DERIVATIVES FOR ENHANCING MUCOSAL ABSORPTION

(75) Inventors: Youngro Byun, Kwangju (KR); Yong-Kyu Lee, Kwangju (KR)

(73) Assignee: Mediplex Corporation, Korea, Seoul (KR)

( * ) Notice: Subject to any disclaimer, the term of this patent is extended or adjusted under 35 U.S.C. 154(b) by 0 days.

(21) Appl. No.: 09/852,131

(22) Filed: May 9, 2001

(65) Prior Publication Data

US 2002/0013292 A1 Jan. 31, 2002

(51) Int. Cl.⁷ ............................................. A61K 31/727
(52) U.S. Cl. .............................. 514/56; 514/54; 514/57; 536/21; 536/17.5; 536/56; 536/92; 536/95; 536/122; 536/123.1; 606/228; 606/231; 604/890.1; 604/891.1
(58) Field of Search ................................ 514/54, 56, 57; 536/21, 17.5, 56, 92, 95, 122, 123.1; 606/228, 231; 604/890.1, 891.1

(56) References Cited

U.S. PATENT DOCUMENTS

| | | | |
|---|---|---|---|
| 4,239,754 A | 12/1980 | Sache et al. | 424/183 |
| 4,857,602 A | 8/1989 | Casey et al. | 525/408 |
| 5,536,508 A | 7/1996 | Canal et al. | 424/501 |
| 5,626,869 A | 5/1997 | Nvqvist et al. | 424/450 |
| 5,700,486 A | 12/1997 | Canal et al. | 424/501 |
| 5,744,155 A | 4/1998 | Friedman et al. | 424/434 |
| 5,820,881 A | 10/1998 | Milstein | 424/489 |
| 5,840,387 A | 11/1998 | Berlowitz-Tarrant et al. | 428/36.91 |
| 5,855,618 A | 1/1999 | Patnaik et al. | 623/11 |
| 5,993,846 A | 11/1999 | Friedman et al. | 424/434 |
| 6,190,591 B1 | 2/2001 | van Lengerich | 264/141 |
| 6,245,753 B1 | 6/2001 | Byun et al. | 514/56 |
| 6,248,363 B1 | 6/2001 | Patel et al. | 424/497 |
| 6,251,428 B1 | 6/2001 | Yoo | 424/455 |

OTHER PUBLICATIONS

A. Leone–Ba, et al.; 4–[4–(2–Hydroxybenzoyl)amino]phenyl butyric Acid as a Novel Oral Delivery Agent for Recombinant Human Growth Hormone, 39 J. Med. Chem. 2571–2578 (1996).
R. Altman, et al.; Oral Anticoagulant Treatment with and without Aspirin, 74(1) F.K. Schattauer Verlagsgesellschaft mbH (Stuttgart) 506–510 (1995).
B. Koefoed, et al., Effect of Fixed Minidose Warfarin, Conventional Dose Warfarin and Aspirin on INR and Prothrombin Fragment 1+2 in Patients with Atrial Fibrillation, 77 (5) F.K. Schattauer Verlagsgesellschaft mbH (Stuttgart) 845–848 (1997).
P. Klement, et al., Hirudin causes more bleeding than heparin in a rabbit ear bleeding model, 132 J. Lab Clin Med 181–185 (1998).
R. Hull, et al.; Hirudin versus heparin and low–molecular–weight heparin: And the winner in . . . , 132 J. Lab Clin Med 151–174 (1998).
G. E. Raskob, Msc. Low molecular weight heparin, heparin, and wafarin, 2 Current Opinion in Hematology 372–379 (1995).
L. Wallentin, Unstable coronary artery disease—need for long term antithrombotic treatment, Aspirin alone is not sufficient, I would associate an anticoagulant, 33 Cardiovascular Research 292–294 (1997).
S. Milstein, et al., Partially unfolded proteins efficiently penetrate cell membranes—implications for oral drug delivery; 53 Journal of Controlled Release 259–267 (1998).
A. Leone–Bay, et al, The evolution of an oral heparin dosing solution, 22(8) Drugs of the Future 885–891 (1997).
A. Leone–Bay, et al., Oral Delivery of Sodium Cromolyn: Preliminary Studies In Vivo and In Vitro, 13(2) Pharmaceutical Research 222–226 (1995).
A. Leone–Bay, et al., N–Acylated α–Amino Acids as Novel Oral Delivery Agents for Proteins, 38 J. Med. Chem. 4263–4269 (1995).
E. Windsor & G. Cronheim, Gastro–Intestinal Absorption of Heparin and Synthetic Heparinoids, 190 Nature 263–264 (1961).
A. Leone–Bay, et al., Acylated non–α–amino acids as novel agents for the oral delivery of heparin sodium, USP, 50 Journal of Controlled Release 41–49 (1998).
D. Brayden, et al., Heparin Absorption Across the Intestine: Effects of Sodium N–[8–(2–Hydroxybenzoyl)Amino] Caprylate in Rat In Situ Intestinal Instillations and in Caco–2 Monolayers, 14(12) Pharmaceutical Research 1772–1779 (1997).
A. Leone–Bay, et al., Synthesis and Evaluation of Compounds That Facilitate the Gastrointestinal Absorption of Heparin, 41 J. Med. Chem 1163–1171 (1998).

(List continued on next page.)

*Primary Examiner*—Kathleen K. Fonda
(74) *Attorney, Agent, or Firm*—Clayton, Howarth & Cannon, P.C.

(57) ABSTRACT

Formulations for enhanced mucosal absorption of heparin are disclosed. In one embodiment, a powdered heparin composition is made by dissolving an amphiphilic heparin derivative including heparin covalently bonded to a hydrophobic agent in a water phase, dispersing the water phase in an organic phase such that an emulsion is formed, and drying the emulsion. In another embodiment, an amorphiphilic heparin derivative dispersed in an oil phase is made by dissolving the amphiphilic heparin derivative in water or a water/organic co-solvent, dispersing the water or co-solvent in the oil phase, and evaporating the water or co-solvent. In another embodiment, heparin-containing nanoparticles having surfactant molecules associated with a hydrophobic agent on the outside of the nanoparticles are made by dissolving the amphiphilic heparin derivative in an aqueous solvent, mixing the surfactant with the aqueous solvent, and disrupting nanoparticles of the amphiphilic heparin derivative. Compositions made according to these methods are also described.

40 Claims, 11 Drawing Sheets

OTHER PUBLICATIONS

A. Leone–Bay, et al., Microsphere Formation in a Series of Derivatized α–Amino Acids: Properties, Molecular Modeling, and Oral Delivery of Salmon Calcitonin, 38 J. Med. Chem 4257–4262 (1995).

Y.–K. Lee et al., Preparation of Slightly Hydrophobic Heparin Derivatives which Can Be Used for Solvent Casting in Polymeric Formulation, 92 Thrombosis Res. 149–156 (1998).

Y.–K. Lee et al., Oral Delivery of New Heparin Derivatives in Rats, 17 Pharma. Res. 1259–1264 (2000).

G.J. Russell–Jones, Carrier–mediated Transport, Oral Drug Delivery, in 1 Controlled Drug Delivery 173–183 (E. Mathiowitz ed. 1999).

P.W. Swaan et al., Enhanced Transepithelial Transport of Peptides by Conjugation to Cholic Acid, 8 Bioconjugate Chem. 520–525 (1997).

Diancourt et al. Journal of Bioactive and Compatible Polymers Jul. 1996, 11(3), 203–218.

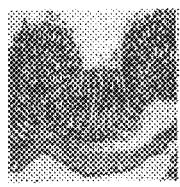 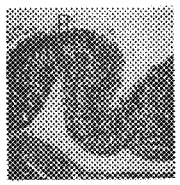 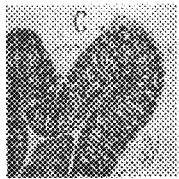 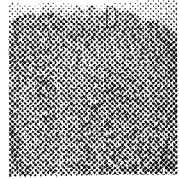 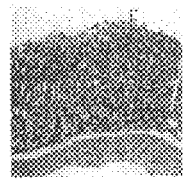
FIG. 5A  FIG. 5B  FIG. 5C  FIG. 5D  FIG. 5E
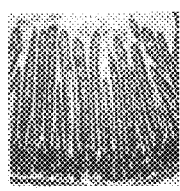 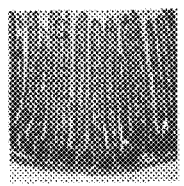 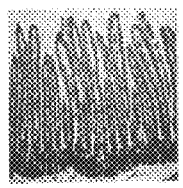 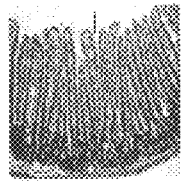 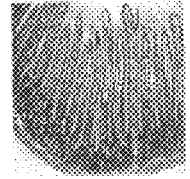
FIG. 5F  FIG. 5G  FIG. 5H  FIG. 5I  FIG. 5J
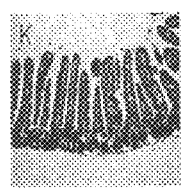 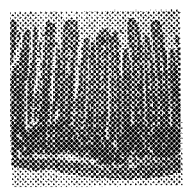 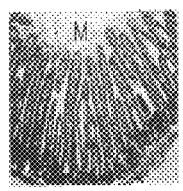 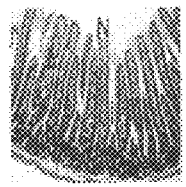 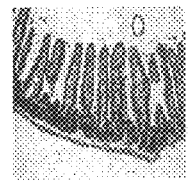
FIG. 5K  FIG. 5L  FIG. 5M  FIG. 5N  FIG. 5O
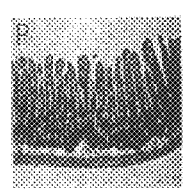 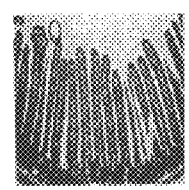 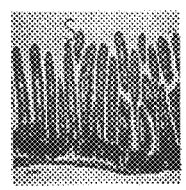 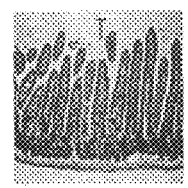 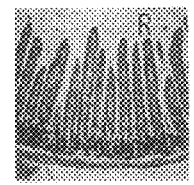
FIG. 5P  FIG. 5Q  FIG. 5S  FIG. 5T  FIG. 5R

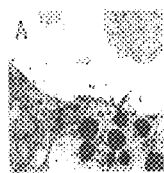 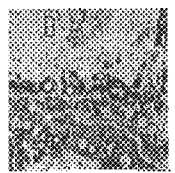 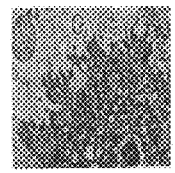 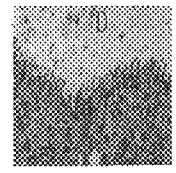 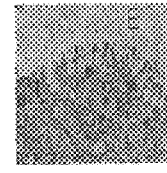
FIG. 7A    FIG. 7B    FIG. 7C    FIG. 7D    FIG. 7E
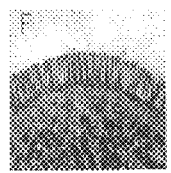 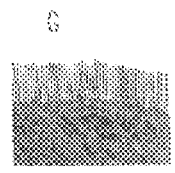 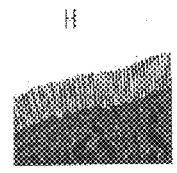 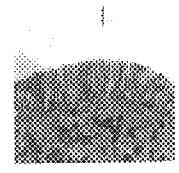 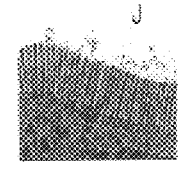
FIG. 7F    FIG. 7G    FIG. 7H    FIG. 7I    FIG. 7J
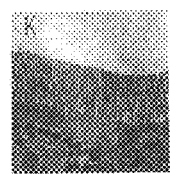 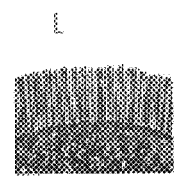 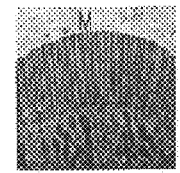 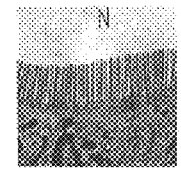 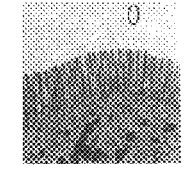
FIG. 7K    FIG. 7L    FIG. 7M    FIG. 7N    FIG. 7O
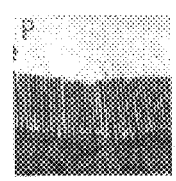 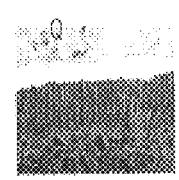 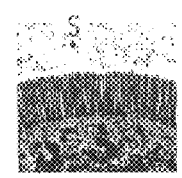 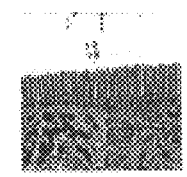 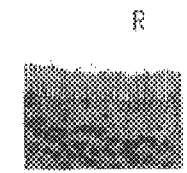
FIG. 7P    FIG. 7Q    FIG. 7S    FIG. 7T    FIG. 7R

 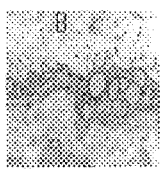 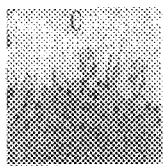 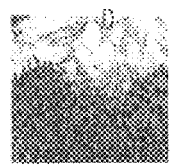 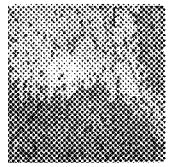
FIG. 8A   FIG. 8B   FIG. 8C   FIG. 8D   FIG. 8E
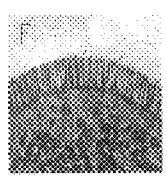 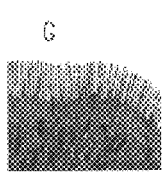 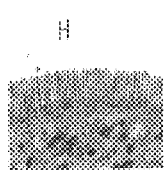 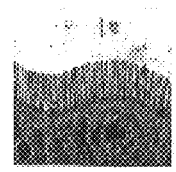 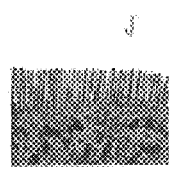
FIG. 8F   FIG. 8G   FIG. 8H   FIG. 8I   FIG. 8J
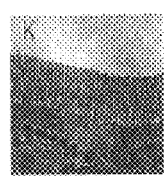 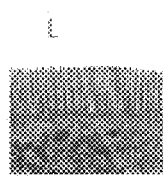 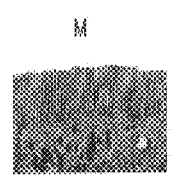 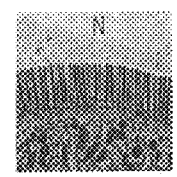 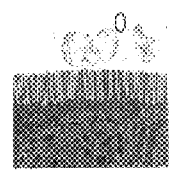
FIG. 8K   FIG. 8L   FIG. 8M   FIG. 8N   FIG. 8O
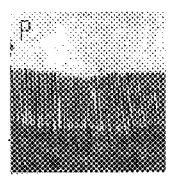 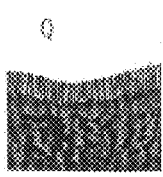 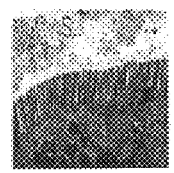 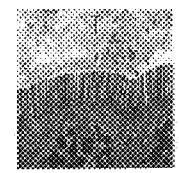 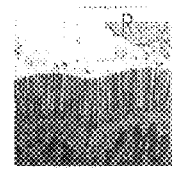
FIG. 8P   FIG. 8Q   FIG. 8S   FIG. 8T   FIG. 8R

FORMULATION OF AMPHIPHILIC HEPARIN DERIVATIVES FOR ENHANCING MUCOSAL ABSORPTION

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

This invention relates to administration of heparin for treating patients in need of anticoagulation therapy. More particularly, this invention relates to formulations of heparin that enhance absorption of heparin through mucosal tissues.

Heparin is widely use as one of the most potent anticoagulants for the treatment and prevention of deep vein thrombosis (DVT) and pulmonary embolism (PE). P. S. Damus et al., Heparin-A Generalized View of its Anticoagulant Action, 246 Nature 355–356 (1973); L. Jin et al., The Anticoagulant Activation of Antithrombin by Heparin, 94 Proc. Nat'l Acad. Sci. USA 14683–14688 (1997). Heparin treatment is limited to hospitalized patients since heparin is given only by injection. R. D. Rosenberg, Biochemistry and Pharmacology of Low Molecular Weight Heparin, 34 Semin. Hematol. 2–8 (1997); G. F. Pineo & R. D. Hull, Unfractionated and Low Molecular-weight Heparin, 82 Curr. Concepts Thromb. 587–599 (1998). Patients are usually switched from intravenous or subcutaneous heparin to oral warfarin upon hospital discharge. Warfarin, however, has a slow onset and is subject to a high possibility of drug-to-drug interactions. There has been a long-felt need for compositions and methods for oral delivery of heparin for the treatment of patients who are at high risk of DVT or PE.

It is known that heparin is not absorbed in the GI tract because of its size and its highly negative charge. L. B. Jaques, Heparins: Anionic Polyelectrolyte Drugs, 31 Pharmacology Rev. 100–166 (1980). The hydrophilic properties of heparin make it difficult to penetrate epithelial cells because of low permeability and repulsion forces of the polar head group of the epithelial membrane. D. A. Norris et al., The Effect of Physical Barriers and Properties on the Oral Absorption of Particulates, 34 Advanced Drug Delivery Reviews 135–154 (1998). While administration of heparin as an aerosol or mixed with lipophilic agents or membrane enhancer agents did not result in detectable plasma heparin levels, A. Dalpozzo et al., New Heparin Complexes Active by Intestinal Absorption. I. Multiple Ion Pairs with Basic Organic Compounds, 56 Thromb. Res. 119–124 (1989), recently, N-[8-(2-hydroxybenzoyl)amino] caprylate (SNAC) was developed as a potent promoter of heparin absorption from the GI tract. R. A. Baughman et al., Oral Delivery of Anticoagulant Doses of Heparin: A Randomized, Double-blind, Controlled Study in Humans, 98 Circulation 1610–1615 (1998).

New heparin derivatives by coupling heparin with hydrophobic agents have been synthesized to increase the hydrophobicity of heparin. Y. Lee, S. H. Kim & Y. Byun, Oral Delivery of New Heparin Derivatives in Rats, 17 Pharm. Res. 1259–1264 (2000); Y. Lee, H. T. Moon & Y. Byun, Preparation of Slightly Hydrophobic Heparin Derivatives Which Can Be Used for Solvent Casting in Polymeric Formulation, 92 Thromb. Res. 149–156 (1998); U.S. patent application Ser. No. 09/300,173, now U.S. Pat. No. 6,245,753. Among those heparin derivatives, a conjugate of heparin and deoxycholic acid (DOCA) demonstrated the highest absorption in the GI tract. Two possibilities were proposed to explain these results: (1) the increased hydrophobicity of heparin due to conjugation with a hydrophobic compound, and (2) the interaction between the coupled DOCA and bile receptors in the ileum.

In view of the foregoing, it will be appreciated that providing formulations that enhance the absorption of heparin through mucosal tissues would be a significant advancement in the art.

BRIEF SUMMARY OF THE INVENTION

It is an advantage of the present invention to provide formulations for enhancing the absorption of heparin through mucosal tissues.

It is also an advantage of the invention to provide formulations for enhancing absorption of heparin through the gastrointestinal mucosa after oral administration.

It is another advantage of the invention to provide methods for administering heparin for enhancing the absorption of heparin through mucosal tissues.

These and other advantages can be addressed by providing a method for making a composition for obtaining enhanced mucosal absorption of heparin comprising:

(a) dissolving an amphiphilic heparin derivative comprising heparin covalently bonded to a hydrophobic agent selected from the group consisting of bile acids, sterols, alkanoic acids, and mixtures thereof in a water phase;

(b) dispersing the water phase containing the dissolved amphiphilic heparin derivative in an organic phase such that an emulsion is formed; and (c) drying the emulsion to result in the composition.

Illustratively, the heparin is a member selected from the group consisting of low molecular weight heparin, high molecular weight heparin, heparin fragments, recombinant heparin, heparin analogs, polysaccharides containing heparin activity, and mixtures thereof.

Another illustrative embodiment of the invention comprises a method for making a composition for obtaining enhanced mucosal absorption of heparin comprising dispersing an amphiphilic heparin derivative comprising heparin covalently bonded to a hydrophobic agent selected from the group consisting of bile acids, sterols, alkanoic acids, and mixtures thereof in an oil phase.

Another illustrative embodiment of the invention comprises a method for making a composition for obtaining enhanced mucosal absorption of heparin comprising:

(a) dissolving an amphiphilic heparin derivative comprising heparin covalently bonded to a hydrophobic agent selected from the group consisting of bile acids, sterols, alkanoic acids, and mixtures thereof in water or a water/organic co-solvent;

(b) dispersing the water or water/organic co-solvent containing the dissolved amphiphilic heparin derivative in an oil phase; and (c) evaporating the water or water/organic co-solvent, resulting in the amphiphilic heparin derivative dispersed in the oil phase.

Still another illustrative embodiment of the invention comprises a method for making a composition for obtaining enhanced mucosal absorption of heparin comprising:

(a) dissolving an amphiphilic heparin derivative comprising heparin covalently bonded to a hydrophobic agent selected from the group consisting of bile acids, sterols, alkanoic acids, and mixtures thereof in a pharmaceutically acceptable aqueous solvent such that the amphiphilic heparin derivative forms nanoparticles in the pharmaceutically acceptable aqueous solvent; and (b) mixing a pharmaceutically acceptable surfactant with the nanoparticles in the pharmaceutically acceptable aqueous solvent and then disrupting the nanoparticles such that the pharmaceutically acceptable surfactant interacts with the heparin and the hydrophobic agent, thereby exposing at least some of the hydrophobic agent on the outside of the nanoparticles.

Illustrative pharmaceutically acceptable surfactants including members selected from the group consisting of anionic surfactants, cationic surfactants, amphoteric surfactants, anionic surfactants, amphiphilic surfactants, hydrophobic surfactants, and mixtures thereof, and the like.

Still another illustrative embodiment of the invention comprises a composition comprising a plurality of an amphiphilic heparin derivative comprising heparin covalently bonded to a hydrophobic agent selected from the group consisting of bile acids, sterols, alkanoic acids, and mixtures thereof, wherein the plurality of the amphiphilic heparin derivative is configured as a nanoparticle having an outer surface such that at least some of the hydrophobic agents are exposed on the outer surface.

Yet another illustrative embodiment of the invention comprises a dosage form comprising a mixture of:

(a) an effective amount of a composition comprising a plurality of an amphiphilic heparin derivative comprising heparin covalently bonded to a hydrophobic agent selected from the group consisting of bile acids, sterols, alkanoic acids, and mixtures thereof, wherein the plurality of the amphiphilic heparin derivative is configured as a nanoparticle having an outer surface such that at least some of the hydrophobic agents are exposed on the outer surface; and (b) a pharmaceutically acceptable carrier.

Another illustrative embodiment of the invention comprises a method for treating a patient in need of anticoagulation therapy comprising administering an effective amount of a composition comprising a plurality of an amphiphilic heparin derivative comprising heparin covalently bonded to a hydrophobic agent selected from the group consisting of bile acids, sterols, alkanoic acids, and mixtures thereof, wherein the plurality of the amphiphilic heparin derivative is configured as a nanoparticle having an outer surface such that at least some of the hydrophobic agents are exposed on the outer surface.

BRIEF DESCRIPTION OF THE SEVERAL VIEWS OF THE DRAWINGS

FIGS. 5A–T show light micrographs of hematoxylin and eosin stained gastrointestinal tissues isolated from mice after oral administration of an admixture of 200 mg/kg HMWH-DOCA conjugate and 200 mg/kg DOCA; FIGS. 5A–E show cross sections of the stomach after 0, 10, 30, 60, and 120 min, respectively; FIGS. 5F–J show cross sections of the duodenum after 0, 10, 30, 60, and 120 minutes, respectively; FIGS. 5K–O show cross sections of the jejunum after 0, 10, 30, 60, and 120 minutes, respectively; and FIGS. 5P–T show cross sections of the ileum after 0, 10, 30, 60, and 120 minutes, respectively; the original magnification was 100× in all micrographs.

FIGS. 6A–T show light micrographs of hematoxylin and eosin stained gastrointestinal tissues isolated from mice after oral administration of an admixture of 200 mg/kg LMWH-DOCA and 200 mg/kg DOCA; FIGS. 6A–E show cross sections of the stomach after 0, 5, 10, 30 and 60 minutes, respectively; FIGS. 6F–J show cross sections of the duodenum after 0, 5, 10, 30 and 60 minutes, respectively; FIGS. 6K–O show cross sections of the jejunum after 0, 5, 10, 30 and 60 minutes, respectively; and FIGS. 6P–T show cross sections of the ileum after 0, 5, 10, 30 and 60 minutes, respectively; the original magnification was 100× in all micrographs.

FIGS. 7A–T show electron micrographs of membrane or microvilli in gastrointestinal tissues isolated from mice after oral administration of an admixture of 200 mg/kg HMWH-DOCA and 200 mg/kg DOCA; FIGS. 7A–E show cross sections of the stomach after 0, 10, 30, 60, and 120 minutes, respectively; FIGS. 7F–J show cross sections of the duodenum after 0, 10, 30, 60, and 120 minutes, respectively; FIGS. 7K–O show cross sections of the jejunum after 0, 10, 30, 60, and 120 minutes, respectively; FIGS. 7P–T show cross sections of the ileum after 0, 10, 30, 60, and 120 minutes, respectively; the original magnification was 25,000× in all micrographs.

FIGS. 8A–T show electron micrographs of membrane or microvilli in gastrointestinal tissues isolated from mice after oral administration of an admixture of 200 mg/kg LMWH-DOCA and 200 mg/kg DOCA: FIGS. 8A–E show cross sections of the stomach after 0, 5, 10, 30 and 60 minutes, respectively; FIGS. 8F–J show cross sections of the duodenum after 0, 5, 10, 30 and 60 minutes, respectively; FIGS. 8K–O show cross sections of the jejunum after 0, 5, 10, 30 and 60 minutes, respectively; FIGS. 8P–T show cross sections of the ileum after 0, 5, 10, 30 and 60 minutes, respectively; the original magnification is 25,000× in all micrographs.

DETAILED DESCRIPTION

Figure 1A:
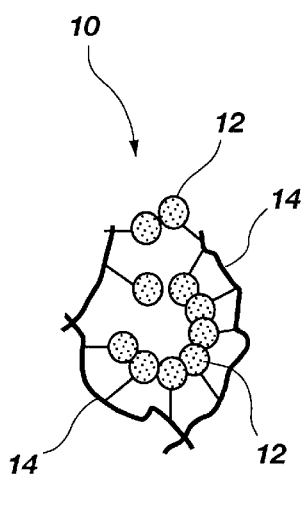
FIGS. 1A–C show schematic diagrams of aggregates or nanoparticles of amphiphilic heparin in an aqueous environment (FIG. 1A), an organic environment (FIG. 1B), and in the presence of surfactant (FIG. 1C).

Before the present formulations and methods for enhancing mucosal absorption of amphiphilic heparin derivatives are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the" include plural referents unless the context clearly dictates otherwise. Thus, for example, reference to "a bile acid" includes a mixture of two or more of such bile acids, reference to "an alkanoic acid" includes reference to one or more of such alkanoic acids, and reference to "a sterol" includes reference to a mixture of two or more sterols.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As used herein, "consisting of" and grammatical equivalents thereof exclude any element, step, or ingredient not specified in the claim.

As used herein, "consisting essentially of" and grammatical equivalents thereof limit the scope of a claim to the specified materials or steps and those that do not materially affect the basic and novel characteristic or characteristics of the claimed invention.

As used herein, "hydrophobic heparin derivative," "amphiphilic heparin derivative," "hydrophobic heparin," and "amphiphilic heparin" are used interchangeably. Heparin is a very hydrophilic material. Increasing the hydrophobicity of heparin by bonding a hydrophobic agent thereto results in what is termed herein as an amphiphilic heparin derivative or hydrophobic heparin derivative. Either term is proper because the heparin derivative has increased hydrophobicity as compared to native heparin and the heparin derivative has a hydrophilic portion and a hydrophobic portion and is, thus, amphiphilic.

As used herein, "bile acids" means natural and synthetic derivatives of the steroid, cholanic acid, including, without limitation, cholic acid, deoxycholic acid, chenodeoxycholic acid, lithocholic acid, ursocholic acid, ursodeoxycholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, hyodeoxycholic acid, and mixtures thereof, and the like.

As used herein, "sterols" means alcohols structurally related to the steroids including, without limitation, cholestanol, coprostanol, cholesterol, epicholesterol, ergosterol, ergocalciferol, and mixtures thereof, and the like.

As used herein, "alkanoic acids" means saturated fatty acids of about 4 to 20 carbon atoms. Illustrative alkanoic acids include, without limitation, butyric acid, valeric acid, caproic acid, caprylic acid, capric acid, lauric acid, myristic acid, palmitic acid, stearic acid, and mixtures thereof, and the like.

As used herein, "HMWH" means high molecular weight heparin, that is, heparin having an average molecular weight of about 12,000 or greater.

As used herein, "LMWH" means low molecular weight heparin, that is, heparin having an average molecular weight of less than about 12,000 and, illustratively, about 6,000 (LMWH(6K)).

As used herein, "W/O emulsion" means a water-in-oil emulsion.

As used herein, "aPTT" means activated partial thromboplastin time, and "FXa" means factor Xa.

As used herein, "DOCA" means deoxycholic acid, and "heparin-DOCA" means a conjugate of heparin and deoxycholic acid. Similarly, "HMWH-DOCA" means a conjugate of high molecular weight heparin and deoxycholic acid, and "LMWH-DOCA" means a conjugate of low molecular weight heparin and deoxycholic acid.

As used herein, "pharmaceutically acceptable" refers to materials and compositions that are physiologically tolerable and do not typically produce an allergic or similar untoward reaction, such as gastric upset, dizziness and the like, when administered to a human. Typically, as used herein, the term "pharmaceutically acceptable" means approved by a regulatory agency of the Federal or a state government or listed in the U.S. Pharmacopeia or other generally recognized pharmacopeia for use in animals, and more particularly in humans.

As used herein, "effective amount" means an amount of a drug or pharmacologically active agent that is nontoxic but sufficient to provide the desired local or systemic effect and performance at a reasonable benefit/risk ratio attending any medical treatment. An effective amount of an amphiphilic heparin derivative as used herein means an amount selected so as to provide the selected amount of anticoagulation activity.

As used herein, the term "carrier" refers to a diluent, adjuvant, excipient, or vehicle with which a composition is administered. Such pharmaceutical carriers can be sterile liquids, such as water and oils, including those of petroleum, animal, vegetable or synthetic origin, such as peanut oil, soybean oil, mineral oil, sesame oil and the like.

As used herein, "tablets" are solid pharmaceutical dosage forms containing drug substances with or without suitable diluents and prepared either by compression or molding methods well known in the art. Tablets have been in widespread use since the latter part of the 19$^{th}$ century and their popularity continues. Tablets remain popular as a dosage form because of the advantages afforded both to the manufacturer (e.g., simplicity and economy of preparation, stability, and convenience in packaging, shipping, and dispensing) and the patient (e.g., accuracy of dosage, compactness, portability, blandness of taste, and ease of administration). Although tablets are most frequently discoid in shape, they may also be round, oval, oblong, cylindrical, or triangular. They may differ greatly in size and weight depending on the amount of drug substance present and the intended method of administration. They are divided into two general classes, (1) compressed tablets, and (2) molded tablets or tablet triturates. In addition to the active or therapeutic ingredient or ingredients, tablets contain a number or inert materials or additives. A first group of such additives includes those materials that help to impart satisfactory compression characteristics to the formulation, including diluents, binders, and lubricants. A second group of such additives helps to give additional desirable physical characteristics to the finished tablet, such as disintegrators, colors, flavors, and sweetening agents.

As used herein, "diluents" are inert substances added to increase the bulk of the formulation to make the tablet a practical size for compression. Commonly used diluents include calcium phosphate, calcium sulfate, lactose, kaolin, mannitol, sodium chloride, dry starch, powdered sugar, silica, and the like.

As used herein, "binders" are agents used to impart cohesive qualities to the powdered material. Binders, or "granulators" as they are sometimes known, impart a cohesiveness to the tablet formulation, which insures the tablet remaining intact after compression, as well as improving the free-flowing qualities by the formulation of granules of desired hardness and size. Materials commonly used as binders include starch; gelatin; sugars, such as sucrose, glucose, dextrose, molasses, and lactose; natural and synthetic gums, such as acacia, sodium alginate, extract of Irish moss, panwar gum, ghatti gum, mucilage of isapol husks, carboxymethylcellulose, methylcellulose, polyvinylpyrrolidone, Veegum, microcrystalline cellulose, microcrystalline dextrose, amylose, and larch arabogalactan, and the like.

As used herein, "lubricants" are materials that perform a number of functions in tablet manufacture, such as improving the rate of flow of the tablet granulation, preventing adhesion of the tablet material to the surface of the dies and punches, reducing interparticle friction, and facilitating the ejection of the tablets from the die cavity. Commonly used lubricants include talc, magnesium stearate, calcium stearate, stearic acid, and hydrogenated vegetable oils. Typical amounts of lubricants range from about 0.1% by weight to about 5% by weight.

As used herein, "disintegrators" or "disintegrants" are substances that facilitate the breakup or disintegration of tablets after administration. Materials serving as disintegrants have been chemically classified as starches, clays, celluloses, algins, or gums. Other disintegrators include Veegum HV, methylcellulose, agar, bentonite, cellulose and wood products, natural sponge, cation-exchange resins, alginic acid, guar gum, citrus pulp, cross-linked polyvinylpyrrolidone, carboxymethylcellulose, and the like.

As used herein, "coloring agents" are agents that give tablets a more pleasing appearance, and in addition help the manufacturer to control the product during its preparation and help the user to identify the product. Any of the approved certified water-soluble FD&C dyes, mixtures thereof, or their corresponding lakes may be used to color tablets. A color lake is the combination by adsorption of a water-soluble dye to a hydrous oxide of a heavy metal, resulting in an insoluble form of the dye.

As used herein, "flavoring agents" vary considerably in their chemical structure, ranging from simple esters, alcohols, and aldehydes to carbohydrates and complex volatile oils. Synthetic flavors of almost any desired type are now available.

The present invention relates to formulations containing heparin derivatives for enhancing the bioavailability of heparin derivatives through a mucosal layer, principally in the gastrointestinal tract, as well as in nasal, pulmonary, rectal, and other mucosal layers.

Three mechanisms for transcellular transport of amphiphilic heparin derivatives have been proposed. One is by partition of amphiphilic heparin derivatives in the mucosal layer due to the hydrophobic nature of the amphiphilic heparin derivative. Another is through interaction of amphiphilic heparin derivatives with bile acid receptors followed by hepato-biliary circulation, especially in the GI tract. The third is that grafted hydrophobic agents attached to the heparin polymer may disorient the cell membrane, thereby enhancing the permeability of amphiphilic heparin derivatives through the mucosal layer. It is unclear which of these proposed mechanisms predominates in the GI tract. It has been shown, however, that the grafted hydrophobic agents, especially bile acids, greatly enhance the absorption of amphiphilic heparin derivatives in the GI tract.

Figure 1B:
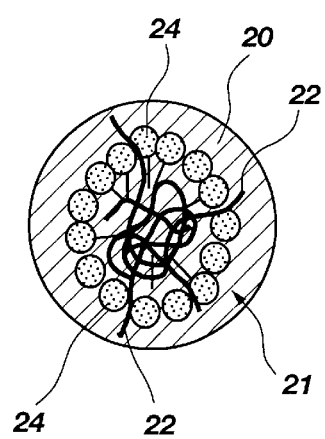

As mentioned above, heparin derivatives can be orally absorbed by the interaction of the coupled hydrophobic agents and the mucosal layer. Therefore, the coupled hydrophobic agents should be exposed to the environment in the GI tract such that interaction with the mucosal layer can more easily be achieved. The GI tract, however, is an aqueous environment, and the coupled hydrophobic agents tend to aggregate and form self-assembled nanoparticles. The structure of such nanoparticles is illustrated in FIG. 1A. These self-assembled nanoparticles 10 of amphiphilic heparin derivatives in aqueous solution have the coupled hydrophobic agents 12 aggregated on the inside of the particle and the hydrophilic heparin 14 located on the outside of the particle. In this configuration it is hard for these heparin derivatives to diffuse through the mucosal layer, because the coupled hydrophobic agents cannot easily interact with the mucosal layer. Therefore, it would be advantageous to provide formulations wherein the structure of such nanoparticles is reversed, that is, wherein the coupled hydrophobic agent is exposed on the surface of the particle and the heparin is contained on the inside of the nanoparticle (i.e., "reverse phase"). Such a structure is illustrated in FIG. 1B, wherein the amphiphilic heparin derivatives are contained in an oil phase 20, resulting in nanoparticles 21 wherein the heparin polymers 22 aggregate in the inside of the particle and the hydrophobic moieties 24 associate with the oil phase on the outside of the particle.

In one illustrative embodiment of the present invention, amphiphilic heparin derivatives are formulated as a powder from a water-in-oil (W/O) emulsion. This formulation is prepared by dissolving the heparin derivatives in a water phase and then dispersing the water phase containing the dissolved heparin derivative in an organic phase as an emulsion. Upon formation of the emulsion, the hydrophobic agents coupled to heparin are exposed to the organic phase and the heparin moieties aggregate in the water phase. The emulsion is then dried, and the heparin derivatives are obtained as a powder having the desired structure, i.e., with the hydrophobic agent exposed on the outside of the particles. This powder of the heparin derivatives can be formulated in conventional dosage forms, such as tablets, capsules, and the like, as is well known in the art. Such formulations of heparin derivatives can be administered orally for absorption by the gastrointestinal mucosa, as well as by other routes for absorption through pulmonary, nasal, buccal, colonic, rectal, and other mucosal tissues.

In another illustrative embodiment of the invention, amphiphilic heparin derivatives can be prepared as dispersions in an oil phase. This formulation is prepared by dissolving the heparin derivatives in water or water/organic co-solvents, followed by dispersing the water or co-solvent in an oil phase. Finally, the water or the co-solvent is evaporated, and the heparin derivatives are dispersed in the oil phase. The resulting composition can then be formulated as a capsule or other conventional dosage form for administering such an oil according to methods well known in the art.

Figure 1C:
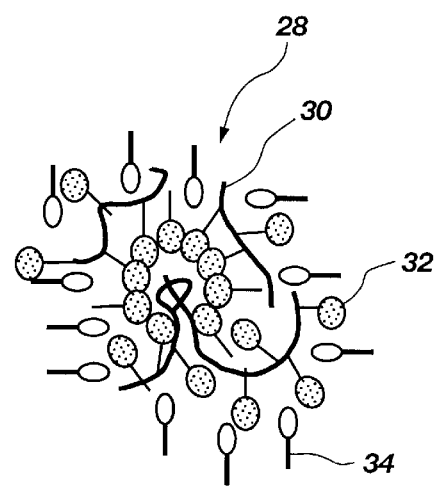

In still another illustrative embodiment of the invention, amphiphilic heparin derivatives are mixed with a surfactant, such as a bile acid, organic surfactant, or other pharmacologically acceptable surfactant, and then the typical nanoparticles are disrupted such that the surfactant molecules can interact with both the heparin moieties and the hydrophobic moieties, thus exposing at least some of the hydrophobic moieties on the surface of the particle. This configuration is illustrated in FIG. 1C, where is shown a nanoparticle 28 comprising heparin moieties 30 and hydrophobic moieties 32, both of which are associated with surfactant molecules 34. Some of the hydrophobic moieties occur on the outside of the particle.

EXAMPLES

Amphiphilic or hydrophobic heparin conjugates used in the examples below were prepared according to the methods disclosed in U.S. Ser. No. 09/300,173, now U.S. Pat. No. 6,245,753, which is hereby incorporated herein in its entirety.

Example 1

Oral Administration of Heparin-DOCA Conjugates with Free DOCA. Mice, housed in the animal care facility at the Korea Animal Center, were fasted for 12 hours before dosing. The mice, weighing 25–30 g, were anesthetized with diethyl ether and were then administered a single oral dose of heparin-DOCA conjugate through an oral gavage that was carefully passed down the esophagus into the stomach. The gavage was made of stainless steel with a blunt end to avoid causing lesions on the tissue surface. Heparin-DOCA conjugate solution was prepared in sodium bicarbonate buffer (pH 7.4). Two kinds of heparin-DOCA conjugates were used in this experiment, (a) HMWH-DOCA conjugate, which contained heparin of molecular weight of about 12,000, and (b) LMWH-DOCA conjugate, which contained heparin of molecular weight of about 6,000. The total administered volume of the heparin-DOCA conjugate solution was 0.4 ml (0.2 ml heparin-DOCA conjugate solution+0.2 ml DOCA). The orally administered amount of heparin-DOCA conjugate was 50 mg/kg, 100 mg/kg, or 200 mg/kg. Blood samples (450 µl) were collected by cardiac puncture at each sampling time and directly mixed with 50 µl of sodium citrate (3.8% solution). The blood samples were immediately centrifuged at 2500×g and 4° C. for 10 minutes. The clotting time and the concentration of heparin-DOCA conjugate in the plasma were measured by aPTT assay and FXa assay, respectively.

Figure 2A:
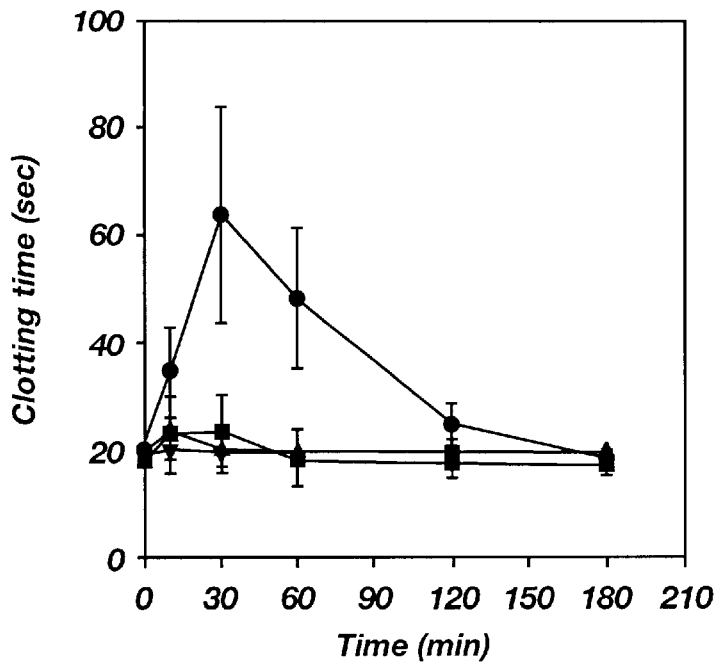
FIGS. 2A and 2B show clotting time profiles measured by aPTT assay (FIG. 2A) and concentration profiles measured by FXa assay (FIG. 2B) after oral administration of heparin-DOCA conjugate in mice: ▼-HMWH, ▲-HMWH-DOCA, ■-HMWH admixed with free DOCA, ●-HMWH-DOCA admixed with free DOCA.
Figure 2B:
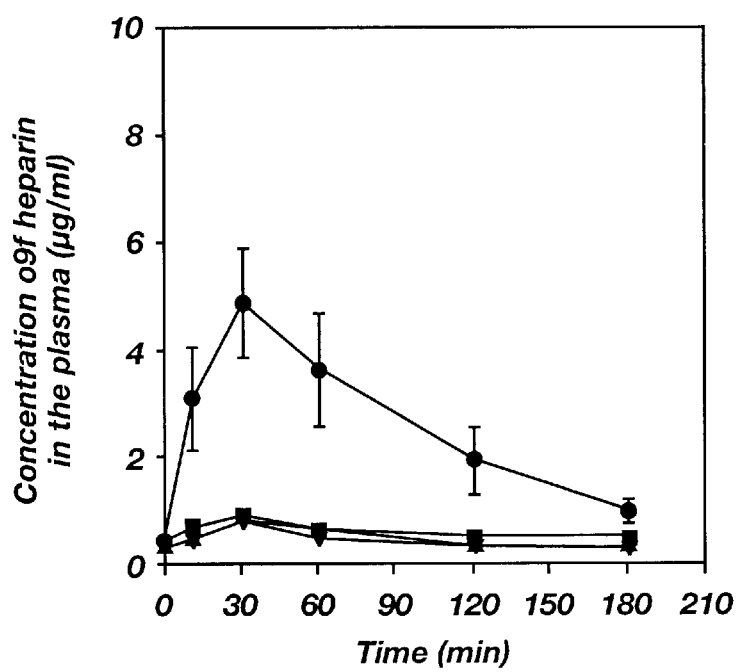
Figure 3A:
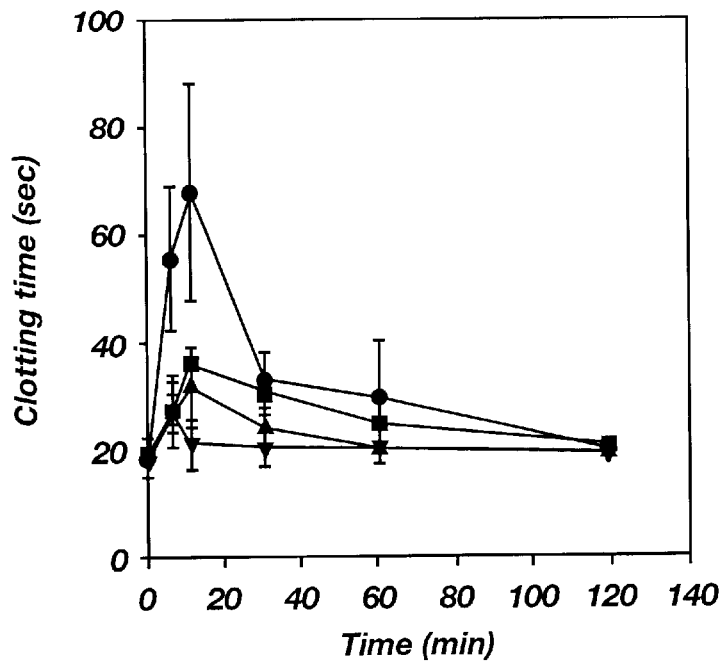
FIGS. 3A and 3B show clotting time profiles measured by aPTT assay (FIG. 3A) and concentration profiles measured by FXa assay (FIG. 3B) after oral administration of heparin-DOCA conjugate in mice: ▼-LMWH, ▲-LMWH-DOCA, ■-LMWH admixed with free DOCA, ●-LMWH-DOCA admixed with free DOCA.
Figure 3B:
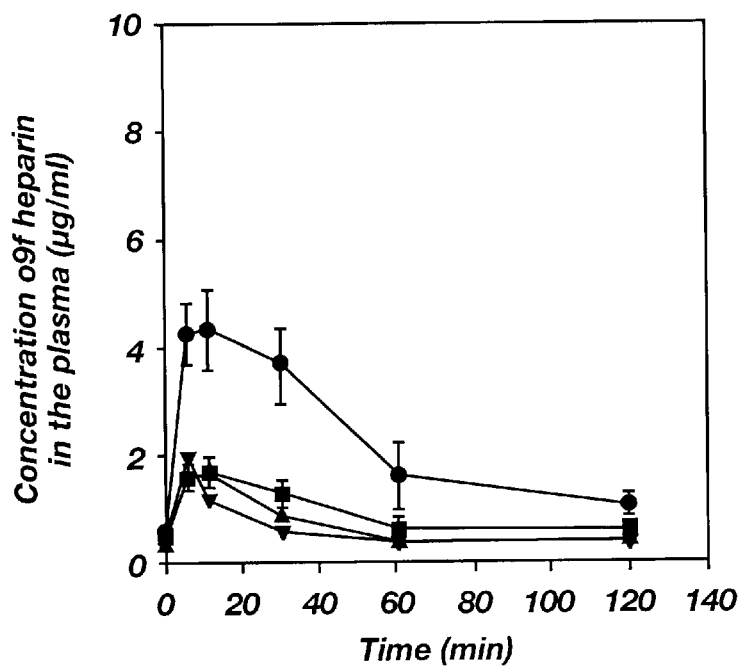

When HMWH, HMWH admixed with DOCA, and HMWH-DOCA were administered orally to mice, respectively, the clotting times in aPTT assay did not change with time in all cases (FIG. 2A). However, when HMWH-DOCA was administered as an admixture with free DOCA, the clotting time increased with time and the maximum clotting time and the peak plasma concentration of HMWH-DOCA were observed at 30 minute (FIGS. 2A–B). When LMWH, LMWH admixed with DOCA, and LMWH-DOCA were administered orally to mice, respectively, the maximum clotting times were about 40 seconds (FIG. 3A). However, when LMWH-DOCA was administered as an admixture with free DOCA, the maximum clotting time and the peak plasma concentration of LMWH-DOCA were increased to as much as 70 seconds and 4 µg/ml, respectively (FIGS. 3A–B).

These results show that oral administration of amphiphilic heparin derivatives is improved when the amphiphilic heparin derivatives are formulated such that hydrophobic groups are present on the outside of aggregates thereof. In this manner, the hydrophobic groups can more easily access mucosal tissues, thus facilitating uptake of the amphiphilic heparin derivatives.

Example 2

Figure 4A:
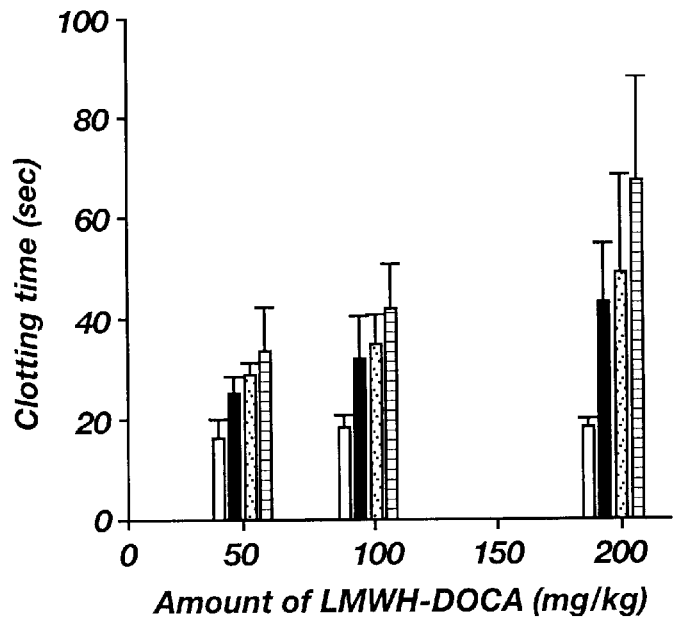
FIGS. 4A and 4B show the dose effect of DOCA admixed with LMWH-DOCA (FIG. 4A) and HMWH-DOCA (FIG. 4B) on clotting time measured by aPTT: open bars—0 mg/kg DOCA, dark bars—33 mg/kg DOCA, shaded bars—100 mg/kg DOCA, segmented bars—200 mg/kg DOCA.
Figure 4B:
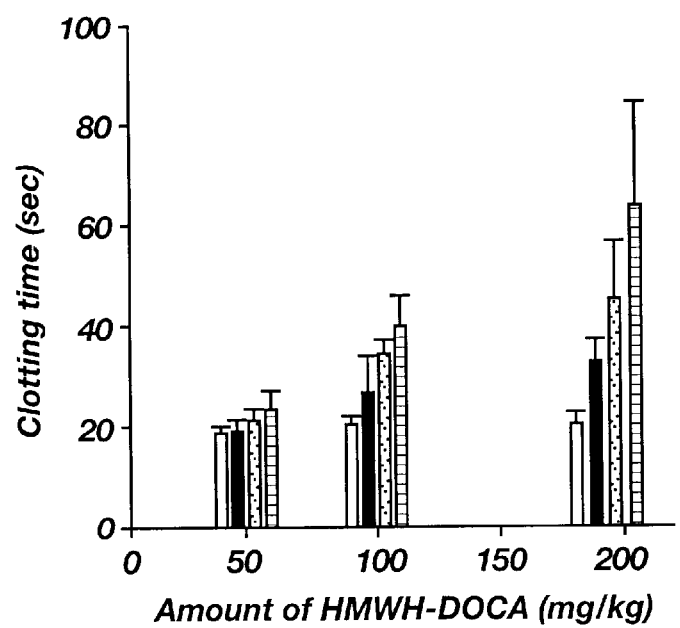

Dose Effect of Free DOCA on Heparin-DOCA Conjugate Absorption in the GI Tract. Heparin-DOCA conjugate solution was prepared in a sodium bicarbonate buffer. The total administered volume of the heparin-DOCA conjugate solution was 0.4 ml (0.2 ml heparin-DOCA conjugate solution+0.2 ml DOCA). The dose amount of heparin-DOCA conjugate was varied from 50 to 200 mg/kg, and the dosage of free DOCA was varied at 33, 100, and 200 mg/kg, respectively. Blood samples (450 µl) were collected at each time and directly mixed with 50 µl of sodium citrate (3.8% solution). The clotting time and the concentration of heparin-DOCA conjugate in the plasma were measured by aPTT assay and FXa assay, respectively. When heparin-DOCA conjugate (200 mg/kg) was orally administered to mice as an admixture with free DOCA, the clotting times increased with the dose amount of free DOCA (FIGS. 4A–B).

Example 3

Histological Evaluation of the Gastrointestinal Tract. Heparin-DOCA conjugate was administered to mice by oral gavage as described in Example 1. The mole ratio of coupled DOCA to heparin in heparin-DOCA conjugate was 10; that is, ten molecules of DOCA were coupled with one molecule of heparin, and the dose amount was 200 mg/kg (including 200 mg/kg DOCA). At 0.5, 1, 2, and 3 hours after dosing with heparin-DOCA conjugate admixed with free DOCA, mice were anesthetized with diethyl ether and were sacrificed by cutting the diaphragm. Gastric, duodenal, jejunal, and ileal tissues were removed from the mice and fixed in neutral buffered formalin for processing. The GI tissues that had not yet been administered heparin-DOCA were prepared as control samples. The tissue specimens were washed with alcohol to remove any water. Specimens were perfused with colored silicone and embedded in paraffin. The embedded specimens were cut into 5 µm-thickness sections using a microtome at −20° C., and were picked up on a glass slide. Each tissue section was then washed with xylene and absolute alcohol, respectively, to remove paraffin. The prepared 5 µm-thickness sections were stained with hematoxylin and eosin (H&E) according to methods well known in the art.

For evaluation by transmission electron microscopy (TEM), gastric, duodenal, jejunal, and ileal tissues were fixed with 1% osmium tetroxide in PBS (0.1 M, pH 7.4), and then were hydrated by changing the alcohol concentration gradually from 50 to 100%. The hydrated tissues were infiltrated with propylene oxide and embedded with epon mixture. The embedded tissues were sectioned and made into 50~60 nm thickness slides. These slides were stained very lightly with uranyl acetate and lead citrate for 1 min, and were observed with a Hitachi 7100 electron microscope (Tokyo, Japan).

In the H&E stain results, no evidence of damage in the GI wall, such as occasional epithelial cell shedding, villi fusion, congestion of mucosal capillary with blood, or focal trauma, were found in any parts of stomach, duodenum, jejunum, or ileum (FIGS. 5A–T and 6A–T). These results confirmed that the increased absorption of heparin-DOCA conjugate was not caused by the disruption of the gastrointestinal epithelium. FIGS. 7A–T and FIGS. 8A–T show the morphology of microvilli by TEM after they were exposed to heparin-DOCA conjugate. The control samples showed healthy tight junctions, microvilli, and mitochondria. After 1, 2, and 3 hours, the cell appearance in all sections showed no damages as microvilli fusion, dissolution, disoriented cell layer with porosity, or cytotoxic effect.

Example 4

Morphologies and Surface Components of Heparin-DOCA Particle. The surface morphology of heparin-DOCA conjugate particles was determined by scanning electron microscopy-energy dispersive electron probe X-ray analysis (SEM-EDX, JEOL JSM-5800 scanning microscopy, Tokyo, Japan). The concentration of sulfur atoms on the particle surfaces of heparin-DOCA conjugate in a dried state was decreased by the mixed free DOCA (Table 1). This result proved that the DOCA moiety coupled to heparin in the heparin-DOCA conjugate could be exposed to the aqueous solution by admixture with free DOCA.

TABLE 1

Surface components of particles of heparin derivatives

| Sample | Atomic % | | |
|---|---|---|---|
| | O | Na | S |
| HMWH | 50.08 ± 0.71 | 20.58 ± 0.71 | 29.33 ± 1.27 |
| HMWH-DOCA | 52.88 ± 0.53 | 19.43 ± 0.11 | 27.02 ± 0.54 |
| HMWH-DOCA + 1.88 mg/ml bile acid | 50.11 ± 1.36 | 26.33 ± 3.08 | 22.92 ± 1.59 |
| HMWH-DOCA + 3.75 mg/ml bile acid | 51.04 ± 2.32 | 23.70 ± 4.12 | 24.48 ± 1.44 |
| HMWH-DOCA + 7.50 mg/ml bile acid | 55.29 ± 2.05 | 25.38 ± 0.19 | 18.59 ± 2.27 |

Example 5

Surface Charges of Heparin-DOCA Particle. Zeta potentials of heparin-DOCA particles in sodium bicarbonate buffer were measured according to procedures well known in the art. Heparin-DOCA conjugate was characterized by negative potentials, as shown in Table 2. The negative potential of heparin-DOCA conjugate particles was decreased by mixing with free DOCA. This was due to the fact that the DOCA moiety coupled to heparin could be exposed on the surface of heparin-DOCA conjugate particles by mixing with free DOCA.

TABLE 2

| Composition | Zeta Potential (mv) |
|---|---|
| Bile Acid | −22.3 ± 11.4 |
| HMWH-DOCA/SB buffer | −55.1 ± 1.01 |
| H-D + 33 mg/kg bile acid | −54.6 ± 1.5 |
| H-D + 100 mg/kg bile acid | −43.3 ± 1.6 |
| H-D + 200 mg/kg bile acid | −45.5 ± 3.25 |

Example 6

Dispersion-type Formulation by Using Sodium Bicarbonate Buffer. First, 1.5 g of sodium bicarbonate was dissolved in 50 ml of PBS buffer (pH 7.4, I=0.15) to prepare a 3% sodium carbonate buffer. The volume of the buffer to be administered into the subject animal was 0.5 ml/kg. Heparin-DOCA conjugate was mixed with the sodium carbonate buffer, and dispersed using the sonication method (80 W, 3 minutes). Heparin-DOCA conjugate dispersed well in the aqueous buffer as nanoparticles.

Example 7

Dispersion-type Formulation Using DOCA as Surfactant. Heparin-DOCA conjugate was dissolved in 3% sodium carbonate buffer. Then, 33, 100, and 200 mg/kg of DOCA were dissolved in distilled water, and sonicated, respectively. After sonication, DOCA solutions were mixed with heparin-DOCA conjugate solution, and sonicated again (80 W) for 3 minutes, respectively. The volume of the buffer to be administered was 0.5 ml/kg.

Example 8

Figure 9:
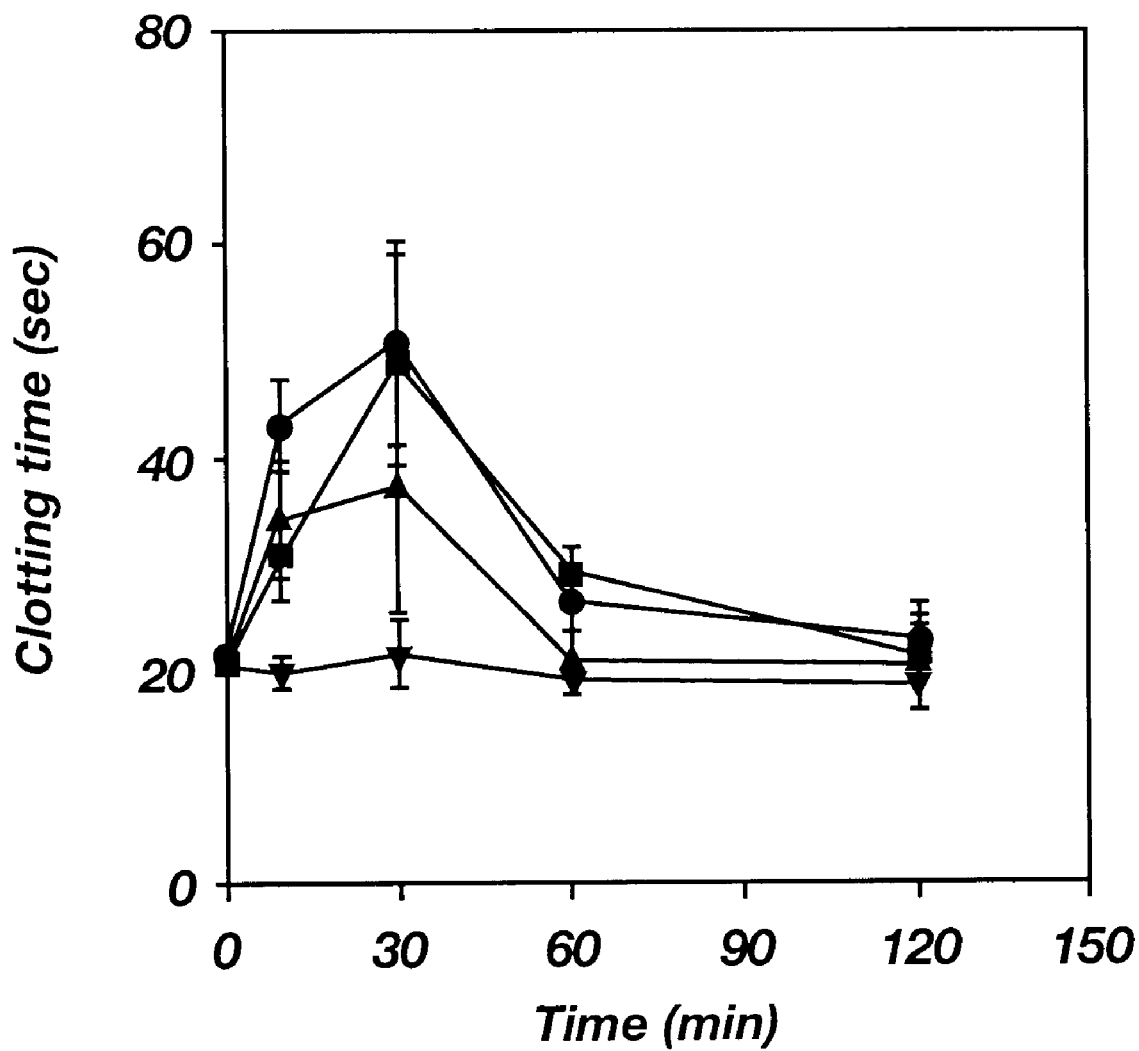
FIG. 9 shows clotting time profiles of heparin-DOCA in selected oils: ▼-squalene, ▲-soybean oil, ■-mineral oil, ●-olive oil.
Figure 10A:
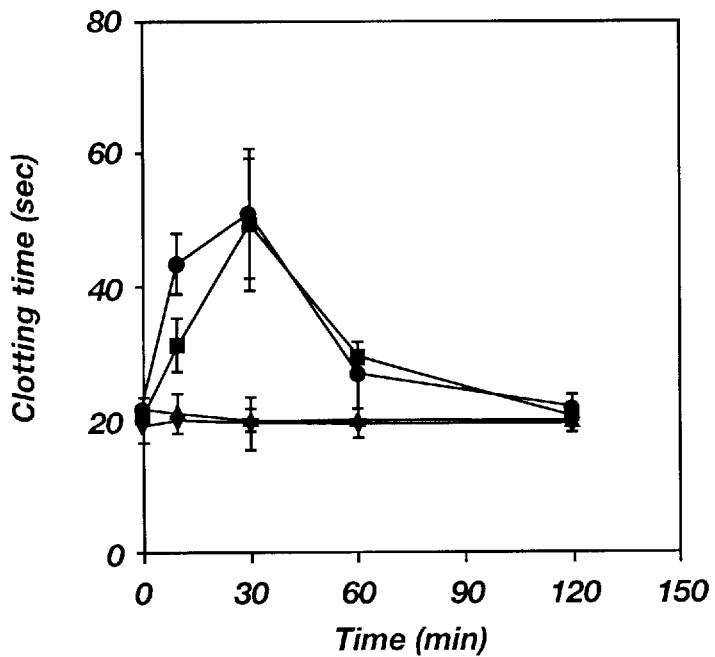
FIG. 10A shows clotting time profiles of high molecular weight heparin or high molecular weight heparin-DOCA in oil or buffer: ▼-HMWH in PBS buffer, ▲-HMWH in olive oil, ■-HMWH-DOCA in mineral oil, ●-HMWH-DOCA in olive oil.
Figure 10B:
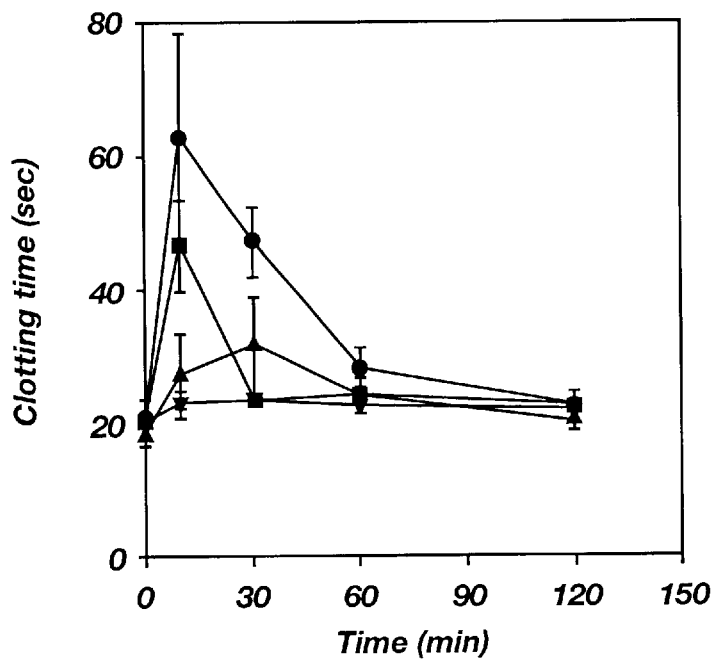
FIG. 10B shows clotting time profiles of low molecular weight heparin or low molecular weight heparin-DOCA in oil or buffer: ▼-LMWH(6K) in olive oil, ▲-LMWH(6K) in PBS buffer, ■-LMWH(6K)-DOCA in mineral oil, ●-LMWH(6K)-DOCA in olive oil.

Dispersion-type Formulation Using Several Oils (Drug/Oil). The amount of heparin-DOCA conjugate was measured according to the weight of mice (Dosage: 200 mg/kg, 100 mg/kg, 50 mg/kg, and 20 mg/kg). Then, the powders of heparin-DOCA conjugate were mixed with soybean oil, mineral oil, olive oil, and squalene, respectively. These dispersions were then homogenized at 15,000 rpm for 10 minutes, respectively. When heparin-DOCA conjugate dispersed in oil was orally administered, the clotting time of heparin-DOCA in olive oil or in mineral oil showed higher clotting time than heparin-DOCA in squalene, as shown in FIG. 9. LMWH(6K)-DOCA also exhibited higher clotting time than LMWH(6K) in olive oil.

Example 9

Dispersion type Formulation Using W/O Emulsification Method 1. First, 100 mg of heparin-DOCA conjugate was dispersed in 10 ml of water by sonicating at 80 W for 3 minutes. Then, 40 ml of Tween 20, 40, 60, and 80 was added, respectively, and then further homogenized at 8,000 rpm for 10 minutes. Water was removed from the resulting emulsions by evaporation under nitrogen flushing at 80° C. To make a further fine emulsion, the preparations were sonicated (80 W, 3 minutes) after removing water.

Example 10

Dispersion-type Formulation Using W/O Emulsification Method 2. First, 100 mg of heparin-DOCA conjugate was dispersed in 10 ml of water by sonicating at 80 W for 3 minutes. Then, 20 ml of Span 20, 40, 60, and 80 was added, respectively, followed by further sonication under the same conditions. The resulting dispersed heparin-DOCA conjugate in oil was dried in vacuum for 24 hours to remove water.

Example 11

Dispersion-type Formulation Using Lyophilized Dry Emulsion Method. Heparin-DOCA conjugate (5–20% w/v) was dispersed in distilled water. Miglyol 812 (10–40%) was added to the dispersion, and a Silverson mixer (Silverson Machines, Waterside, UK) was used at 8,000–12,000 rpm for preparing an emulsion having good morphological properties. The dispersed heparin-DOCA and Miglyol 812 in aqueous medium appeared as a milky phase. Next, 50 ml of 2-propanol was used to remove the Miglyol 812 at –10° C. for 20 min. The heparin-DOCA conjugate was then dried under reduced pressure for 24 hrs to remove water. The resulting emulsion (0.8 gm) was put in PVE blisters of 15 mm diameter and 6 mm length. These PVE blisters were sonicated for 3 min at 80W.

Example 12

Dispersion-type Formulation by Using Lyophilized Dry Emulsion Method with Surfactant. Heparin-DOCA conjugate (5–20% w/v) and free DOCA were dispersed in distilled water. Miglyol 812 (10–40%) was then added to the dispersion, and a Silverson mixer (Silverson Machines, Waterside, UK) was used for preparing an emulsion at 15,000 rpm for 15 minutes. Next, 50 ml of 2-propanol was used to remove the Miglyol 812 at –10° C. for 20 minutes. The resulting heparin-DOCA conjugate mixed with free DOCA was then dried under reduced pressure for 24 hours to remove water. These emulsions (0.8 g) were next mixed with soybean oil, mineral oil, olive oil and squalene, respectively, and homogenized at 15,000 rpm for 10 minutes, respectively.

Example 13

Figure 11:
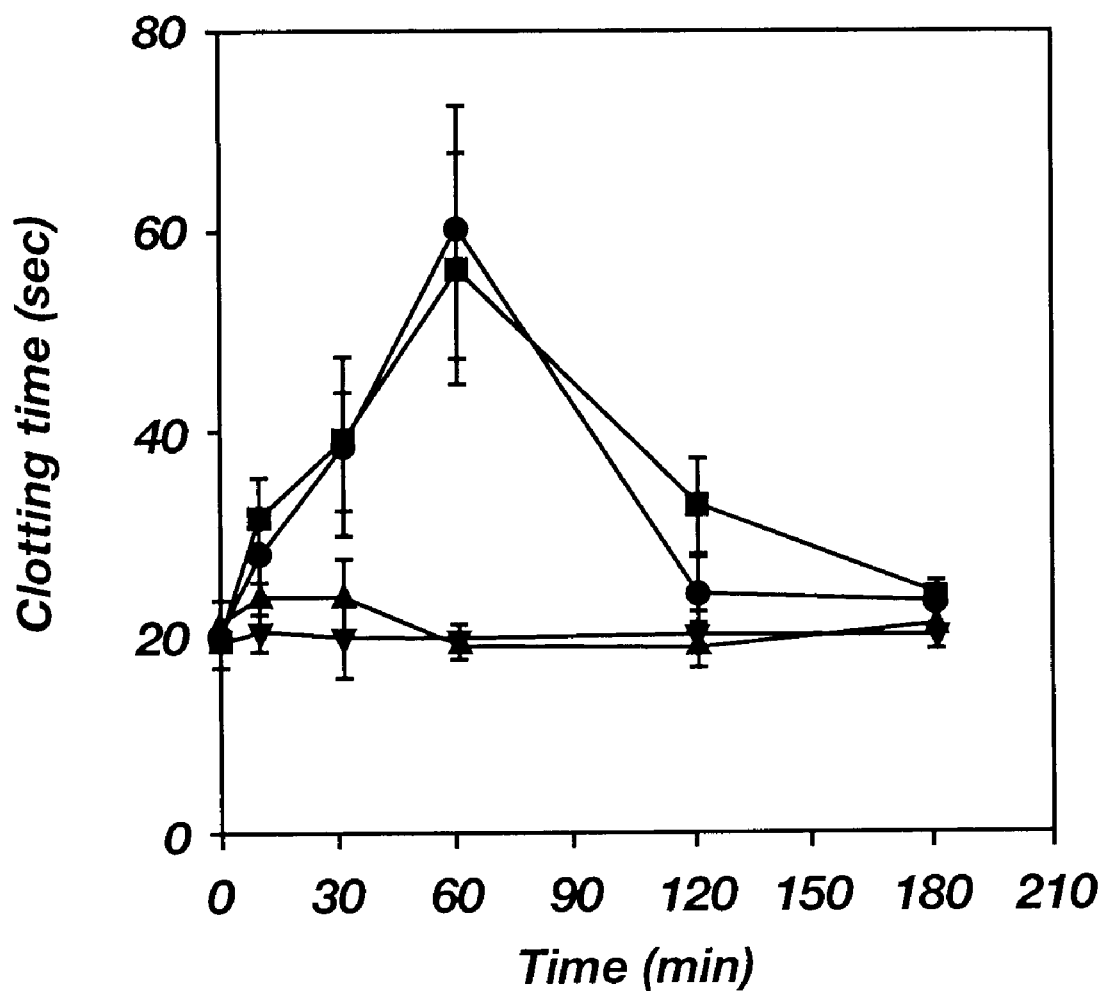
FIG. 11 shows clotting time profiles of heparin-DOCA in oil after emulsification in a W/O emulsion: ▼-HMWH in PBS buffer, ▲-HMWH in olive oil, ■-HMWH-DOCA in mineral oil, ●-HMWH-DOCA in olive oil.

Preparation of Reverse-phase Heparin-DOCA Conjugate Powder. First, 50 mg of heparin-DOCA conjugate was dispersed in 2 ml of water. Next, 10 ml HCO-60 (5%, polyoxyethylene hydrogenated castor oil derivative) was added and homogenized at 8,000 rpm for 10 minutes. The emulsion was collected and 10 ml isopropanol was used to remove the HCO-60 at 10° C. After stirring for 10 minutes, the emulsion was filtered (0.45 mm membrane filter), and the filtrate was dried in a freeze-drier for 24 hours. When unmodified heparin in olive oil or PBS buffer was orally administered to mice as controls, the clotting time did not increase. On the other hands, when the heparin-DOCA in olive oil or mineral oil was orally administered to mice, the clotting time increased as shown in FIG. 11.

Example 14

Tablet-type Formulation of Reverse-phase Heparin-DOCA Conjugate Using Sorbital. First, sorbital (3 vol) and reverse-phased heparin-DOCA conjugate powder, which was prepared according to the procedure of Example 13, were mixed. The mixture was weighed, and a binder was added slowly (1 μl binder solution/10 mg). For this procedure, 7.5% polyvinylpyrrolidone was used as a binder, with 25% ethanol. The powder and granulates were mixed with the binder and 1% lubricant (magnesium stearate). After measuring the concentration of the solution, it was placed inside a press kit (400 pounds) and pressure was applied. The tablets were prepared and dried at room temperature.

Example 15

Tablet-type Formulation of Reverse-phase Heparin-DOCA Conjugate Using Sorbital and DOCA. Sorbital (3 vol), deoxycholic acid, and reverse-phased heparin-DOCA conjugate powder were mixed. The mixture was weighed, and a binder was added slowly (1 ml binder solution/10 mg). For this procedure, 7.5% polyvinylpyrrolidone was used as a binder, with 25% ethanol. The powder and granulates were mixed with the binder and 1% lubricant (magnesium stearate). After measuring the concentration of the solution, it was put inside a press kit (400 pounds) and pressure was applied. The tablets were prepared and dried at room temperature.

Example 16

Tablet type Formulation of Reverse-phase Heparin-DOCA Conjugate Using Biphasic Release Tablet Method. A diluent such as cornstarch was mixed with reverse-phase heparin-DOCA conjugates, and 1% methylcellulose solution was added. The solution was then filtered using a 25-mesh sieve, and dried at 40° C. A given amount of disintegrants was added to induce rapid release in the GI tract. Polyvinylpyrrolidone and sodium starch glycolate were used as disintegrants. A minute amount of magnesium stearate and colloidal silicon dioxide were added to the preparation and stirred for 15 minutes. Several different concentrations of hydroxypropylmethylcellulose (HPMC) were mixed with the solution to form an extended release layer.

Example 17

Tablet-type Formulation of Reverse-phase Heparin-DOCA Conjugate Using Biphasic Release Tablet Method with DOCA(surfactant). A diluent such as cornstarch and deoxycholic acid were mixed with reverse-phased heparin-DOCA conjugates, and 1% methylcellulose solution was added. The solution was then filtered using a 25-mesh sieve, and dried at 40° C. A given amount of disintegrants was added to induce rapid release in the GI tract. Polyvinylpyrrolidone and sodium starch glycolate were used as disintegrants. A minute amount of magnesium stearate and colloidal silicon dioxide were added to the solution and stirred for 15 minutes. Several different concentrations of HPMC were mixed with the solution to form an extended release layer.

Example 18

Tablet-type Formulation of Reverse-phase Heparin-DOCA Conjugate Using Granulate Method. Reverse-phase heparin conjugates (heparin-DOCA was strained through a 0.04 or 0.027 inch sieve. Polyvinylpyrrolidone (MW: 1 million, PVP), which was stirred for 15 min, and a binder were added to the solution and mixed together. The stirred material and the binder took up 3.4% of the total mixture. The mixture was pressed with a compacter at a pressure of 50 KN to form tablets.

Example 19

Tablet-type Formulation of Reverse-phase Heparin-DOCA Conjugate Gelatin Capsule Filled with Powder. Hard gelatin capsules were filled with deoxycholic acid and reverse-phase heparin-DOCA conjugates. After capsules were sealed using 5% (w/w) ethanolic solution, they were coated again using the spray method. Eudragit E100 (acrylic polymer; Rohm Pharm, Darmstadt, Germany), hydroxypropylmethylcellulose, and hydroxypropylmethylcellulose acetate succinate (HPMC-AS) were used for coatings.

Example 20

Tablet-type Formulation of Reverse-phase Heparin-DOCA Conjugate Gelatin Capsule Filled with Solution.

Reverse-phase heparin-DOCA conjugate (100 mg) was dispersed in 10 ml mineral oil by sonicating for 3 minutes at the speed of 80 W. Then, the resulting solution was put inside gelatin capsules and sealed.

Example 21

Enteric Coating Formulation of Reverse-phase Heparin-DOCA Conjugate by Using Eudragit L100. First, Eudragit L 100 (8 w/v % solution) was dissolved in isopropanol-acetone(1.7:1 v/v). Reverse-phase heparin-DOCA conjugates and bile acid were mixed, and then tablets were synthesized and coated with the enteric coating. Sorbital and heparin-DOCA conjugates (1 vol) were mixed. This mixture was weighed, and a binder (1 μl binder solution/10 mg) was added slowly to the mixture. For this procedure, 7.5% polyvinylpyrrolidone was used as a binder, with 25% ethanol. After measuring the concentration of the solution, it was placed inside a press kit (400 pounds) and pressure was applied. Tablets were prepared and dried at room temperature. Using a single solution, these tablets were dip coated three times, and dried at room temperature for 20 minutes.

Example 22

Dispersion-type Formulation of Reverse-phase Heparin-DOCA Conjugate The powders of reverse-phase heparin-DOCA conjugate were mixed with soybean oil, mineral oil, olive oil and squalene, respectively. These mixtures were homogenized at 15, 000 rpm for 10 minutes, respectively. This procedure resulted in heparin-DOCA conjugate dispersed in oil.

The subject matter claimed is:

1. A method for making a composition for obtaining enhanced mucosal absorption of heparin comprising:
   (a) dissolving an amphiphilic heparin derivative comprising heparin covalently bonded to a hydrophobic agent selected from the group consisting of bile acids, sterols, alkanoic acids, and mixtures thereof in a water phase;
   (b) dispersing the water phase containing the dissolved amphiphilic heparin derivative in an organic phase such that an emulsion is formed; and
   (c) drying the emulsion to result in the composition.

2. The method of claim 1 wherein said hydrophobic agent is a bile acid selected from the group consisting of cholic acid, deoxycholic acid, chenodeoxycholic acid, lithocholic acid, ursocholic acid, ursodeoxycholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, hyodeoxycholic acid, and mixtures thereof.

3. The method of claim 2 wherein said bile acid is deoxycholic acid.

4. The method of claim 1 wherein said hydrophobic agent is a sterol selected from the group consisting of cholestanol, coprostanol, cholesterol, epicholesterol, ergosterol, ergocalciferol, and mixtures thereof.

5. The method of claim 1 wherein said hydrophobic agent is an alkanoic acid comprising about 4 to 20 carbon atoms.

6. The method of claim 5 wherein said alkanoic acid is a member selected from the group consisting of butyric acid, valeric acid, caproic acid, caprylic acid, capric acid, lauric acid, myristic acid, palmitic acid, stearic acid, and mixtures thereof.

7. The method of claim 1 wherein said heparin is a member selected from the group consisting of low molecular weight heparin, high molecular weight heparin, heparin fragments, recombinant heparin, heparin analogs, polysaccharides containing heparin activity, and mixtures thereof.

8. A method for making a composition for obtaining enhanced mucosal absorption of heparin comprising dispersing an amphiphilic heparin derivative comprising heparin covalently bonded to a hydrophobic agent selected from the group consisting of bile acids, sterols, alkanoic acids, and mixtures thereof in an oil phase.

9. The method of claim 8 wherein said hydrophobic agent is a bile acid selected from the group consisting of cholic acid, deoxycholic acid, chenodeoxycholic acid, lithocholic acid, ursocholic acid, ursodeoxycholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, hyodeoxycholic acid, and mixtures thereof.

10. The method of claim 9 wherein said bile acid is deoxycholic acid.

11. The method of claim 8 wherein said hydrophobic agent is a sterol selected from the group consisting of cholestanol, coprostanol, cholesterol, epicholesterol, ergosterol, ergocalciferol, and mixtures thereof.

12. The method of claim 8 wherein said hydrophobic agent is an alkanoic acid comprising about 4 to 20 carbon atoms.

13. The method of claim 12 wherein said alkanoic acid is a member selected from the group consisting of butyric acid, valeric acid, caproic acid, caprylic acid, capric acid, lauric acid, myristic acid, palmitic acid, stearic acid, and mixtures thereof.

14. The method of claim 8 wherein said heparin is a member selected from the group consisting of low molecular weight heparin, high molecular weight heparin, heparin fragments, recombinant heparin, heparin analogs, polysaccharides containing heparin activity, and mixtures thereof.

15. The method of claim 8 wherein said oil phase is a pharmaceutically acceptable oil.

16. A method for making a composition for obtaining enhanced mucosal absorption of heparin comprising:
   (a) dissolving an amphiphilic heparin derivative comprising heparin covalently bonded to a hydrophobic agent selected from the group consisting of bile acids, sterols, alkanoic acids, and mixtures thereof in water or a water/organic co-solvent;
   (b) dispersing the water or water/organic co-solvent containing the dissolved amphiphilic heparin derivative in an oil phase; and
   (c) evaporating the water or water/organic co-solvent, resulting in the amphiphilic heparin derivative dispersed in the oil phase.

17. The method of claim 16 wherein said hydrophobic agent is a bile acid selected from the group consisting of cholic acid, deoxycholic acid, chenodeoxycholic acid, lithocholic acid, ursocholic acid, ursodeoxycholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, hyodeoxycholic acid, and mixtures thereof.

18. The method of claim 17 wherein said bile acid is deoxycholic acid.

19. The method of claim 16 wherein said hydrophobic agent is a sterol selected from the group consisting of cholestanol, coprostanol, cholesterol, epicholesterol, ergosterol, ergocalciferol, and mixtures thereof.

20. The method of claim 16 wherein said hydrophobic agent is an alkanoic acid comprising about 4 to 20 carbon atoms.

21. The method of claim 20 wherein said alkanoic acid is a member selected from the group consisting of butyric acid, valeric acid, caproic acid, caprylic acid, capric acid, lauric acid, myristic acid, palmitic acid, stearic acid, and mixtures thereof.

22. The method of claim 16 wherein said heparin is a member selected from the group consisting of low molecular weight heparin, high molecular weight heparin, heparin fragments, recombinant heparin, heparin analogs, polysaccharides containing heparin activity, and mixtures thereof.

23. The method of claim 16 wherein said oil phase is a pharmaceutically acceptable oil.

24. A method for making a composition for obtaining enhanced mucosal absorption of heparin comprising:
(a) dissolving an amphiphilic heparin derivative comprising heparin covalently bonded to a hydrophobic agent selected from the group consisting of bile acids, sterols, alkanoic acids, and mixtures thereof in a pharmaceutically acceptable aqueous solvent such that said amphiphilic heparin derivative forms nanoparticles in said pharmaceutically acceptable aqueous solvent; and
(b) mixing a pharmaceutically acceptable surfactant with said nanoparticles in said pharmaceutically acceptable aqueous solvent and then disrupting said nanoparticles such that said pharmaceutically acceptable surfactant interacts with the heparin and the hydrophobic agent, thereby exposing at least some of the hydrophobic agent on the outside of the nanoparticles.

25. The method of claim 24 wherein said hydrophobic agent is a bile acid selected from the group consisting of cholic acid, deoxycholic acid, chenodeoxycholic acid, lithocholic acid, ursocholic acid, ursodeoxycholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, hyodeoxycholic acid, and mixtures thereof.

26. The method of claim 25 wherein said bile acid is deoxycholic acid.

27. The method of claim 24 wherein said hydrophobic agent is a sterol selected from the group consisting of cholestanol, coprostanol, cholesterol, epicholesterol, ergosterol, ergocalciferol, and mixtures thereof.

28. The method of claim 24 wherein said hydrophobic agent is an alkanoic acid comprising about 4 to 20 carbon atoms.

29. The method of claim 28 wherein said alkanoic acid is a member selected from the group consisting of butyric acid, valeric acid, caproic acid, caprylic acid, capric acid, lauric acid, myristic acid, palmitic acid, stearic acid, and mixtures thereof.

30. The method of claim 24 wherein said heparin is a member selected from the group consisting of low molecular weight heparin, high molecular weight heparin, heparin fragments, recombinant heparin, heparin analogs, polysaccharides containing heparin activity, and mixtures thereof.

31. The method of claim 24 wherein said pharmaceutically acceptable surfactant is a member selected from the group consisting of anion surfactants, cationic surfactants, amphoteric surfactants, anionic surfactants, amphiphilic surfactants, hydrophobic surfactants, and mixtures thereof.

32. The method of claim 31 wherein said pharmaceutically acceptable surfactant is a bile acid.

33. The method of claim 32 wherein said bile acid is deoxycholic acid.

34. A composition prepared according to the method of claim 1.

35. A composition prepared according to the method of claim 8.

36. A composition prepared according to the method of claim 16.

37. A composition prepared according to the method of claim 24.

38. A composition comprising a plurality of an amphiphilic heparin derivative comprising heparin covalently bonded to a hydrophobic agent selected from the group consisting of bile acids, sterols, alkanoic acids, and mixtures thereof, wherein said plurality of the amphiphilic heparin derivative is configured as a nanoparticle having an outer surface such that at least some of the hydrophobic agents are exposed on the outer surface.

39. A dosage form comprising a mixture of:
(a) an effective amount of a composition comprising a plurality of an amphiphilic heparin derivative comprising heparin covalently bonded to a hydrophobic agent selected from the group consisting of bile acids, sterols, alkanoic acids, and mixtures thereof, wherein said plurality of the amphiphilic heparin derivative is configured as a nanoparticle having an outer surface such that at least some of the hydrophobic agents are exposed on the outer surface; and
(b) a pharmaceutically acceptable carrier.

40. A method for treating a patient in need of anticoagulation therapy comprising administering an effective amount of a composition comprising a plurality of an amphiphilic heparin derivative comprising heparin covalently bonded to a hydrophobic agent selected from the group consisting of bile acids, sterols, alkanoic acids, and mixtures thereof, wherein said plurality of the amphiphilic heparin derivative is configured as a nanoparticle having an outer surface such that at least some of the hydrophobic agents are exposed on the outer surface.

* * * * *